United States Patent
Lee et al.

(10) Patent No.: US 12,322,756 B2
(45) Date of Patent: Jun. 3, 2025

(54) ELECTROLYTE SOLUTION FOR LITHIUM SECONDARY BATTERY AND LITHIUM SECONDARY BATTERY INCLUDING SAME

(71) Applicants: HYUNDAI MOTOR COMPANY, Seoul (KR); KIA CORPORATION, Seoul (KR); UNIST (ULSAN NATIONAL INSTITUTE OF SCIENCE AND TECHNOLOGY), Ulsan (KR)

(72) Inventors: Yoon Sung Lee, Suwon-si (KR); Jun Ki Rhee, Suwon-si (KR); Ko Eun Kim, Cheongju-si (KR); Sung Ho Ban, Hwaseong-si (KR); Seung Min Oh, Incheon (KR); Sung You Hong, Ulsan (KR); Sang Kyu Kwak, Ulsan (KR); Nam Soon Choi, Ulsan (KR); Hyeong Jun Kim, Ulsan (KR); Hui Beom Nam, Ulsan (KR); Min Ho Jeon, Ulsan (KR)

(73) Assignees: HYUNDAI MOTOR COMPANY, Seoul (KR); KIA CORPORATION, Seoul (KR); UNIST (ULSAN NATIONAL INSTITUTE OF SCIENCE AND TECHNOLOGY), Ulsan (KR)

(*) Notice: Subject to any disclaimer, the term of this patent is extended or adjusted under 35 U.S.C. 154(b) by 559 days.

(21) Appl. No.: 17/870,046

(22) Filed: Jul. 21, 2022

(65) Prior Publication Data
US 2023/0207875 A1    Jun. 29, 2023

(30) Foreign Application Priority Data

Dec. 29, 2021 (KR) .................. 10-2021-0191208

(51) Int. Cl.
*H01M 10/0567* (2010.01)
*C07C 309/87* (2006.01)
(Continued)

(52) U.S. Cl.
CPC ....... *H01M 10/0567* (2013.01); *C07C 309/87* (2013.01); *H01M 4/505* (2013.01);
(Continued)

(58) Field of Classification Search
CPC ......... H01M 10/0567; H01M 10/0568; H01M 10/0569; H01M 2300/0025;
(Continued)

(56) References Cited

U.S. PATENT DOCUMENTS

| | | | |
|---|---|---|---|
| 9,595,737 | B2 | 3/2017 | Shimamoto et al. |
| 2023/0207876 | A1* | 6/2023 | Lee ................... H01M 10/0568 429/338 |

FOREIGN PATENT DOCUMENTS

| | | |
|---|---|---|
| CN | 111883842 A | 11/2020 |
| EP | 2821395 A2 | 1/2015 |

(Continued)

OTHER PUBLICATIONS

Alberto Marra, et al. (2018). Protein Glycosylation through Sulfur Fluoride Exchange (SuFEx) Chemistry: The Key Role of a Fluorosulfate Thiolactoside. Chemistry A European Journal, 24:18981-18987.

*Primary Examiner* — Kevin E Yoon
(74) *Attorney, Agent, or Firm* — MCDONNELL BOEHNEN HULBERT & BERGHOFF LLP

(57) ABSTRACT

An additive for an electrolyte solution improves the electrochemical properties of a lithium secondary battery.

10 Claims, 4 Drawing Sheets

(51) Int. Cl.
    *H01M 4/505*     (2010.01)
    *H01M 4/525*     (2010.01)
    *H01M 10/052*     (2010.01)
    *H01M 10/0568*     (2010.01)
    *H01M 10/0569*     (2010.01)
    *H01M 4/02*     (2006.01)

(52) U.S. Cl.
    CPC ......... *H01M 4/525* (2013.01); *H01M 10/052* (2013.01); *H01M 10/0568* (2013.01); *H01M 10/0569* (2013.01); *H01M 2004/028* (2013.01); *H01M 2300/0025* (2013.01); *H01M 2300/0028* (2013.01); *H01M 2300/004* (2013.01)

(58) Field of Classification Search
    CPC . H01M 2300/0028; H01M 2300/0031; H01M 2300/0034; H01M 2300/0037; H01M 2300/004; H01M 2300/0042
    See application file for complete search history.

(56) References Cited

FOREIGN PATENT DOCUMENTS

| | | | | |
|---|---|---|---|---|
| EP | 3772130 A1 | 2/2021 | | |
| KR | 10-1264435 B1 | 5/2013 | | |
| KR | 2016-0141667 A | 12/2016 | | |
| WO | 2017/102557 A1 | 6/2017 | | |
| WO | WO-2019111983 A1 * | 6/2019 | .......... | H01M 10/052 |
| WO | 2021/006238 A1 | 1/2021 | | |

* cited by examiner

ELECTROLYTE SOLUTION FOR LITHIUM SECONDARY BATTERY AND LITHIUM SECONDARY BATTERY INCLUDING SAME

CROSS REFERENCE TO RELATED APPLICATIONS

The present application claims priority to Korean Patent Application No. 10-2021-0191208, filed Dec. 29, 2021, the entire contents of which is incorporated herein for all purposes by this reference.

BACKGROUND

1. Field

The present disclosure relates to an electrolyte solution constituting a lithium secondary battery and to a lithium secondary battery including the same. Specifically, the present disclosure relates to an additive for an electrolyte solution to improve the electrochemical properties of a lithium secondary battery.

2. Description of the Related Art

Batteries are energy storage sources capable of converting chemical energy into electrical energy or electrical energy into chemical energy. Batteries can be divided into non-reusable primary batteries and reusable secondary batteries. Compared to primary batteries which are used once and discarded, secondary batteries are eco-friendly compared because they can be reused.

Recently, as environmental problems have emerged, the demand for hybrid electric vehicle (HEV) and electric vehicle (EV) with little or no air pollution is increasing. In particular, EVs are vehicles in which the internal combustion engine has been completely removed, suggesting the future direction the world should take.

A lithium secondary battery is used as an energy source for EVs. A lithium secondary battery is largely composed of a cathode, an anode, an electrolyte, and a separator. In the cathode and anode, intercalation and deintercalation of lithium ions are repeated to generate energy, an electrolyte becomes a path for lithium ions to move, and in the separator, the cathode and anode meet to prevent a short circuit in a battery.

In particular, the cathode is closely related to the capacity of the battery, and the anode is closely related to the performance of the battery such as high-speed charging and discharging.

The electrolyte is composed of a solvent, an additive, and a lithium salt. The solvent becomes a transport channel that helps lithium ions move back and forth between the cathode and the cathode. In order for a battery to have good performance, lithium ions must be rapidly transferred between the cathode and the anode. Therefore, selecting an optimal electrolyte is very important in order to obtain excellent battery performance.

In particular, a thin film called solid electrolyte interphase (SEI) is formed on the anode in the chemical conversion process performed during the production process of the battery. SEI is a membrane that can pass lithium ions but not electrons and prevents battery performance from degrading because electrons pass through SEI and induce additional reactions. In addition, the SEI suppresses the direct reaction of the electrolyte and the anode and suppresses the separation of the anode.

The additive of the electrolyte is a substance added in a trace amount of 0.1 to 10% with respect to the weight of the electrolyte. Despite the trace amount added, the performance and stability of the battery are greatly affected by the additives. In particular, the additive induces the formation of SEI on the surface of the anode and plays a role in controlling the thickness of the SEI. In addition, the additive can prevent the battery from being overcharged and can increase the conductivity of lithium ions in the electrolyte.

On the other hand, the energy density of lithium secondary batteries largely depends on the characteristics of cathode and anode materials, and it is necessary to develop a suitable electrolyte for the developed cathode and anode materials to exhibit excellent electrochemical performance.

Recently, in NCM-based oxide, which is a high-capacity cathode active material, the cathode capacity may be increased by increasing the Ni content or the high voltage of the charging voltage, but the residual lithium ($Li_2CO_3$ and LiOH) components on the surface of the cathode accelerate electrolyte decomposition and also increase a degradation rate due to an increase in interface reactivity with the electrolyte, thereby degrading a lithium secondary battery and rapidly degrading electrochemical performance.

Therefore, it is necessary to introduce an additive capable of forming an electrochemically and chemically stable SEI.

The matters described as the background art above are only for improving the understanding of the background of the present disclosure and should not be accepted as acknowledging that they correspond to the related art already known to those of ordinary skilled in the art.

SUMMARY

The present disclosure has been proposed to solve these problems, and an objective of the present disclosure is to provide an electrolyte solution additive capable of improving the electrochemical properties of a lithium secondary battery by being added to the electrolyte solution of a lithium secondary battery.

The present disclosure relates to an electrolyte for a lithium secondary battery containing an electrolyte salt and an organic solvent, the electrolyte contains vinylene carbonate (VC) represented by the following Formula 1, and the electrolyte further includes an additive, 4-(allyloxy)phenyl fluoro sulfate, represented by the following Formula 2.

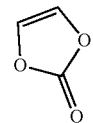

Formula 1

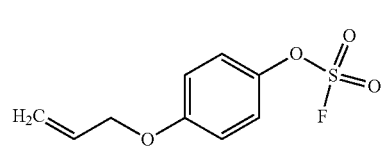

Formula 2

4-(allyloxy)phenyl fluoro sulfate may be included in an amount of 0.1 to 1.0% by weight with respect to the total weight of the electrolyte.

VC may be included in an amount of 0.1 to 10% by weight with respect to the total weight of the electrolyte.

Electrolyte salts may be mixed with any one or two or more compounds selected from the group consisting of $LiPF_6$, $LiBF_4$, $LiClO_4$, $LiCl$, $LiBr$, $LiI$, $LiB_{10}Cl_{10}$, $LiCF_3SO_3$, $LiCF_{3.0}CO_2$, $Li(CF_3SO_2)_{3.0}C$, $LiAsF_6$, $LiSbF_6$, $LiAlCl_4$, $LiCH_3SO_3$, $LiCF_3SO_3$, $LiN(SO_{2.0}C_2F_5)_2$, $Li(CF_3SO_2)_2N$, $LiC_4F_9SO_3$, $LiB(C_6H_5)_4$, and $Li(SO_2F)_2N$ (LiFSI).

The electrolyte salt may be included in a concentration of 0.5 M to 1.0 M.

The organic solvent may be any one or two or more of solvents selected from the group consisting of a carbonate-based solvent, an ester-based solvent, an ether-based solvent, and a ketone-based solvent.

The lithium secondary battery, including the electrolyte solution, includes a cathode, an anode, and a separator interposed between the cathode and the anode, and the cathode of the lithium secondary battery may include a nickel-cobalt-manganese (NCM)-based cathode active material, at this time, nickel, cobalt, and manganese may have a ratio of 6:2:2 to 8:1:1.

According to the present disclosure, when a lithium secondary battery is manufactured using an electrolyte using additive 1 and additive 2, additive 2 firmly forms CEI and SEI in the cathode and anode, thereby obtaining a lithium secondary battery with increased electrochemical characteristics.

DETAILED DESCRIPTION

Hereinafter, specific contents for solving the above-described objective and problems will be described in detail with reference to the accompanying drawings. On the other hand, when the detailed description of a known technology in the same field is not helpful in understanding the core content of the disclosure in understanding the present disclosure, the description will be omitted, and the technical spirit of the present disclosure is not limited thereto and may be variously implemented by being changed by those skilled in the art.

One feature of the present disclosure is that the electrochemical properties of a lithium secondary battery may be increased by using vinylene carbonate (VC) represented by Formula 1 as an additive and 4-(allyloxy)phenyl fluoro sulfate represented by Formula 2 as an additive, simultaneously.

Formulae 1 and 2 are as follows.

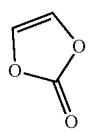

Formula 1

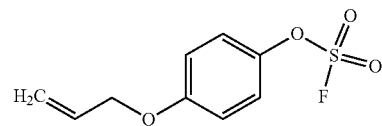

Formula 2

Hereinafter, VC will be represented as additive 1, and 4-(allyloxy)phenyl fluoro sulfate will be represented as additive 2.

By using additive 1 and additive 2 simultaneously, cathode electrolyte interphase (CEI) is formed on the cathode, and SEI is formed on the anode, thereby improving the lifespan and output characteristics of the battery.

Specifically, since additive 2 has a low LUMO energy level and a high HOMO energy level compared to other materials included in the electrolyte, it is expected to react first on the cathode and anode surfaces to form CEI and SEI.

Figure 1:
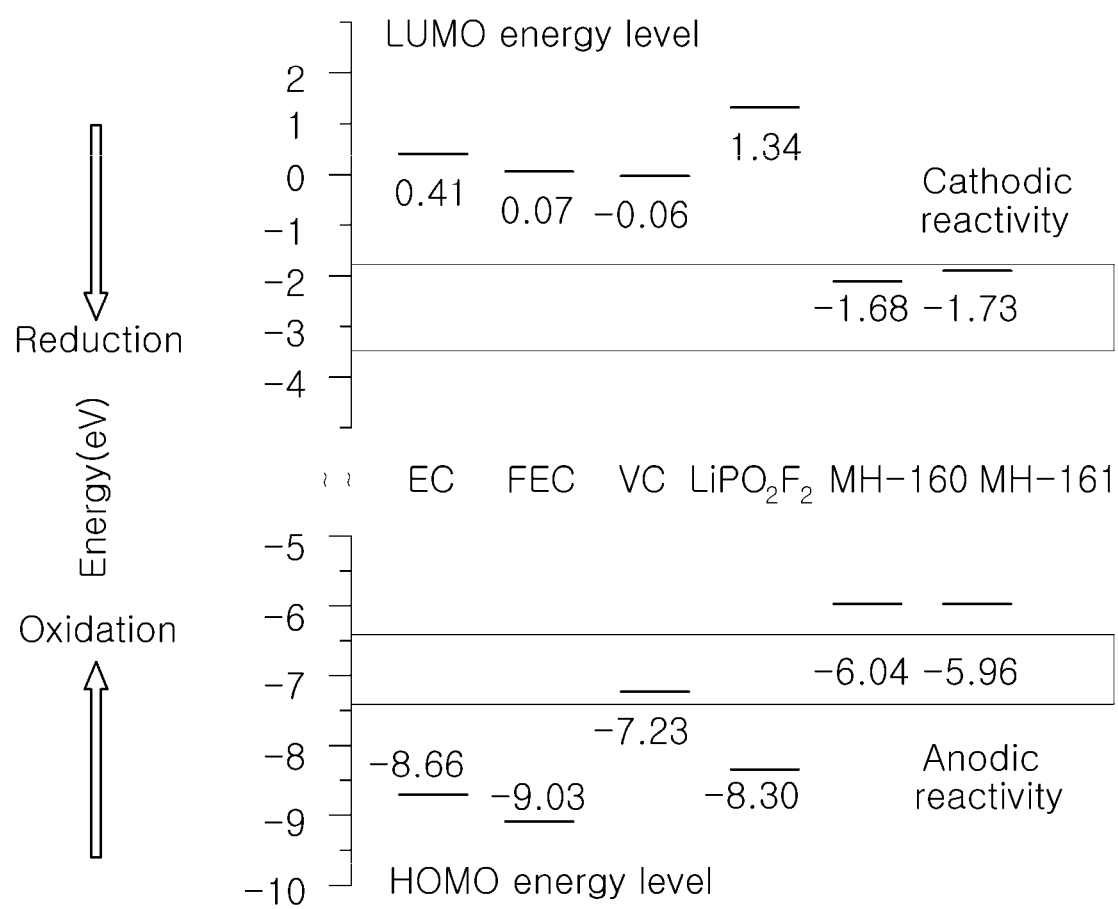
FIG. 1 is a graph showing the energy levels of HOMO and LUMO of 4-(allyloxy)phenyl fluoro sulfate.

FIG. 1 shows the energy levels corresponding to LUMO and HOMO of additive 2, and MH-161 corresponds to additive 2 of the present disclosure. Referring to FIG. 1, the HOMO energy level of additive 2 is −5.96 eV, and the energy level of LUMO is −1.73 eV, and it may be expected that the reaction will occur as it is easily decomposed at the cathode and the anode than EC and FEC used as solvents, VC used as additives, and $LiPO_2F_2$.

In particular, the formation of a film can be expected by inducing radical polymerization through the vinyl group at the end of the additive 2. The polymer formed as described above is a polymer component and may have physical flexibility, thereby suppressing breakage of a film structure due to volume expansion and contraction caused by an anode problem, and a phenomenon in which the film is continuously thickened due to breakage of the film structure and the resulting exposure of the cathode active material.

In addition, the molecules are dissociated in the electrolyte to have $OSO_2^{2-}$ functional groups and are expected to form SEI of $Li_2SO_3$ and $ROSO_2Li$ components. The sulfone-based components such as $Li_2SO_3$ and $ROSO_2Li$ are expected to play a role in improving electrochemical properties by forming a film having low resistance and excellent thermal stability.

In addition, fluorine (F) bonded to the molecular end is expected to form LiF on the surface of the anode, and additive 2 is expected to be more effective in forming LiF because fluorine has a higher deintercalation tendency than other additives, fluoroethylene carbonate (FEC), (The binding energy of the C—F bond inside the FEC is −1.61 eV, and the binding energy of the S—F bond inside the additive 2 is −4.35 eV).

On the other hand, additive 2 of the present disclosure may be prepared through the following mechanism:

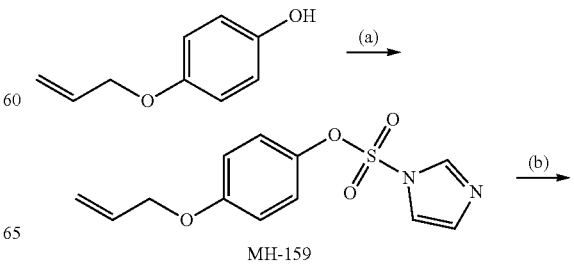

MH-159

-continued

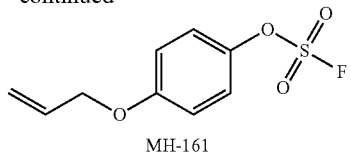

MH-161

(a) 1,1°-Sulfonyldiimidazole (1.5 equiv), Cs₂CO₃ (0.5 equiv), THF, rt, 12 h
(b) AgF (1.8 equiv), MeCN, 80° C., 12 h ① 04.50 ml, 29.96 mmol of 4-(allyloxy)phenol and 4.88 g, 14.98 mmol of cesium carbonate are dissolved in 45 ml of tetrahydrofuran, and 8.91 g, 44.95 mmol of 1.1'-sulfonyl diimidazole is added.

② After the mixture was stirred at room temperature for 12 hours, 4-(allyloxy)phenyl 1H-imidazole-1-sulfonate (MH-159) in the form of a transparent oil was obtained through column chromatography (ethyl acetate/hexanes: 3/7)(93% yield, 7.78 g).

As a result of H-NMR, it was confirmed that MH-159 could be obtained by obtaining the following result values:

$^1$H NMR (300 MHz, CDCl₃) δ 7.71 (t, J=1.0 Hz, 1H), 7.28 (t, J=1.5 Hz, 1H), 7.16 (dd, J=1.6, 0.8 Hz, 1H), 6.86-6.79 (m, 4H), 6.01 (ddt, J=17.3, 10.5, 5.3 Hz, 1H), 5.39 (dq, J=17.3, 1.6 Hz, 1H), 5.30 (dq, J=10.5, 1.4 Hz, 1H), 4.50 (dt, J=5.3, 1.5 Hz, 2H).

$^{13}$C{$^1$H} NMR (101 MHz, CDCl₃) δ 158.4, 142.5, 137.7, 132.6, 131.4, 122.4, 118.5, 118.3, 116.0, 69.3.

③ 7.78 g, 27.76 mmol of MH-159 was dissolved in 100 ml of acetonitrile, 6.34 g, 49.97 mmol of silver(I) fluoride was added, and the mixture was stirred at 80° C. for 12 hours, and then 4-(allyloxy)phenyl fluoro sulfate(MH-161) in the form of yellow oil can be obtained through column chromatography (ethyl acetate/hexanes: 3/7) (90% yield, 5.80 g).

As a result of H-NMR, it was confirmed that MH-161 could be obtained by obtaining the following result values.

$^1$H NMR (400 MHz, CDCl₃) δ 7.29-7.21 (m, 3H), 7.01-6.91 (m, 2H), 6.04 (ddt, J=17.3, 10.5, 5.3 Hz, 1H), 5.42 (dq, J=17.3, 1.6 Hz, 1H), 5.32 (dq, J=10.5, 1.4 Hz, 1H), 4.55 (dt, J=5.3, 1.5 Hz, 2H). $^{19}$F{$^1$H}NMR (377 MHz, CDCl₃) δ 36.4.

Hereinafter, the results of experiments on electrochemical properties by manufacturing a lithium secondary battery using the additive will be described.

The cathode includes an NCM-based cathode active material made of Ni, Co, and Mn, and in particular, NCM811 was used in this embodiment. As the cathode active material may be used of LiCoO₂, LiMnO₂, LiNiO₂, LiNi$_{1-x}$Co$_x$O₂, LiNi$_{0.5}$Mn$_{0.5}$O₂, LiMn$_{2-x}$M$_x$O₄ (M is Al, Li or a transition metal), LiFePO, and the like, and all other cathode active materials that can be used for lithium secondary batteries may be used.

The cathode may further include a conductive material and a binder.

The conductive material is used to impart conductivity to an electrode. Any electronically conductive material without causing chemical changes in a configured battery can be used as a conductive material. For example, natural graphite, artificial graphite, carbon black, acetylene black, Ketjen black, carbon fiber, metal powder such as copper, nickel, aluminum, silver, metal fiber, and the like can be used as a conductive material, and one type or a mixture of one or more types of conductive materials including polyphenylene derivatives may be used.

The binder serves to adhere the particles of the active material well to each other or to the current collector, which is to mechanically stabilize the electrode. That is, the active material is stably fixed in the process of repeated intercalation and deintercalation of lithium ions to prevent the loosening of the bond between the active material and the conductive material. The binder may include polyvinyl alcohol, carboxymethyl cellulose, hydroxypropyl cellulose, diacetyl cellulose, polyvinyl chloride, carboxylated polyvinyl chloride, polyvinyl fluoride, a polymer including ethylene oxide, polyvinylpyrrolidone, polyurethane, polytetrafluoro ethylene, polyvinylidene fluoride, polyethylene, polypropylene, styrene-butadiene rubber, acrylated styrene-butadiene rubber, epoxy resin, nylon, and the like, but is not limited thereto.

The anode includes any one or more of carbon (C)-based or silicon (Si)-based anode active material, and the carbon-based anode material may include one or more of materials selected from the group consisting of artificial graphite, natural graphite, graphitized carbon fiber, graphitized mesocarbon microbeads, fullerene, and amorphous carbon, and the silicon-based anode active material may include any one of SiO$_x$ and silicon-carbon composite materials. In particular, a graphite anode active material was used in this embodiment.

Like the cathode, the anode may further include a binder and a conductive material.

The electrolyte solution is composed of an organic solvent and additives.

The organic solvent may include any one or two or more solvents selected from the group consisting of a carbonate-based solvent, an ester-based solvent, an ether-based solvent, and a ketone-based solvent.

At this time, the carbonate-based solvent may include dimethyl carbonate (DMC), diethyl carbonate (DEC), dipropyl carbonate (DPC), methyl propyl carbonate (MPC), ethyl propyl carbonate (EPC), ethyl methyl carbonate (EMC), ethylene carbonate (EC), propylene carbonate (PC), butylene carbonate (BC), fluoroethylene carbonate (FEC), vinylene carbonate (VC), and the like. In addition, γ-butyrolactone (GBL), n-methyl acetate, n-ethyl acetate, n-propyl acetate, and the like may be used as the ester-based solvent, and dibutyl ether may be used as the ether-based solvent but is not limited thereto.

The solvent may further include an aromatic hydrocarbon-based organic solvent. Specific examples of the aromatic hydrocarbon-based organic solvent may include alone or in combination of benzene, fluorobenzene, bromobenzene, chlorobenzene, cyclohexylbenzene, isopropyl benzene, n-butylbenzene, octyl benzene, toluene, xylene, mesitylene, and the like.

The separator prevents a short circuit between the cathode and anode and provides a passage for lithium ions to move. Such separators may include known materials such as polyolefin-based polymer membrane such as polypropylene, polyethylene, polyethylene/polypropylene, polyethylene/polypropylene/polyethylene, and polypropylene/polyethylene/polypropylene, or multilayers thereof, microporous films, woven fabrics, and non-woven fabrics. In addition, a film coated with a resin having excellent stability on the porous polyolefin film may be used.

Preparation and Experiment of Batteries Corresponding to Comparative Examples and Examples
Preparation of Cathode
For the preparation of the cathode, PVdF was dissolved in NMP to prepare a binder solution.
A slurry was prepared by mixing the cathode active material, and Ketjen Black used as a conductive material in a binder solution. The slurry was coated on both sides of an aluminum foil and dried.
After that, a rolling process and a drying process were performed, and the aluminum electrode was ultrasonically welded to prepare a cathode. In the rolling process, the thickness was adjusted to be 120 μm to 150 μm.
In this case, $Li[Ni_{1-x-y}Co_xMn_y]O_2$ (1-x-y≥0.6), a material in which Ni, Co, and Mn were mixed in the ratio of an 8:1:1, was used as the cathode active material.
Preparation of Anode
A slurry was prepared by mixing the anode active material, and Ketjen Black used as a conductive material in a binder solution. The slurry was coated on both sides of an aluminum foil and dried.
After that, a rolling process and a drying process were performed, and the aluminum electrode was ultrasonically welded to prepare a cathode. In the rolling process, the thickness was adjusted to be 120 μm to 150 μm.
At this time, graphite was used as the anode active material.
Preparation of Electrolyte Solution
A mixture of ethylene carbonate (EC), ethylmethyl carbonate (EMC), and diethyl carbonate (DEC) in a volume ratio of 25:45:30 was used as an organic solvent, and 0.5 M $LiPF_6$ and 0.5 M LiFSI were dissolved in the solvent as lithium salts, and the electrolyte was injected. In addition, according to each Example, different ratios of additive 2 were added to the organic solvent.
Preparation of Coin Cell
After interposing a separator between the cathode and the anode, and then wound to prepare a jelly roll. A coin cell was prepared using the prepared jelly roll and electrolyte.

Comparative Example 1

Only additive 1 (1.0% by weight) was used as an additive in the electrolyte, and it is a lithium secondary battery that does not include additive 2.

Comparative Example 2

It is a lithium secondary battery using an electrolyte solution further including additive 1 (1.0% by weight) and $LiPO_2F_2$ (0.5% by weight) as an additive.

Example 1

It is a lithium secondary battery using an electrolyte solution including additive 1 (1.0% by weight) and additive 2 (0.1% by weight).

Example 2

It is a lithium secondary battery using an electrolyte solution further including additive 1 (1.0% by weight) and additive 2 (0.5% by weight).

Example 3

It is a lithium secondary battery using an electrolyte solution including additive 1 (1.0% by weight) and additive 2 (0.1% by weight).

For Comparative Examples 1 to 2 and Examples 1 to 3, the results of measuring the cell initial charging and discharging efficiency, the lifespan characteristics after 100 cycles of charging and discharging at a high temperature (45° C.), and the rate-specific characteristics at a high rate (2 C-rate) are shown in Tables 1, 2 and 3.

TABLE 1

|  | Additives (% by weight) | | | Cell initial efficiency |
| --- | --- | --- | --- | --- |
|  | Additive 1 | $LiPO_2F_2$ | Additive 2 | (%) |
| <Comparative Example 1> | 1.0. | — | — | 96.4% |
| <Comparative Example 2> | 1.0. | 0.5. | — | 96.5% |
| <Example 1> | 1.0. | — | 0.1. | 92.5% |
| <Example 2> | 1.0. | — | 0.5. | 97.1% |
| <Example 3> | 1.0. | — | 1.0. | 92.5% |

Table 1 shows the cell initial efficiencies for Comparative Examples and Examples, and the cell initial efficiency refers to a value obtained by dividing a discharge capacity by a charge capacity after charging once after the manufacturing of a lithium secondary battery is completed, discharging is performed, and then discharging is performed. The cut-off voltage was set to 2.5 V to 4.2 V, and the C-rate was tested at 1C at 45° C.

As a result of the experiment, in the case of Example 2 in which 0.1% by weight of additive 2 was added, it was confirmed that the initial cell efficiency was the best. In the case of Examples 1 and 3, experimental results were found to be inferior to those of the comparative example.

Figure 2:
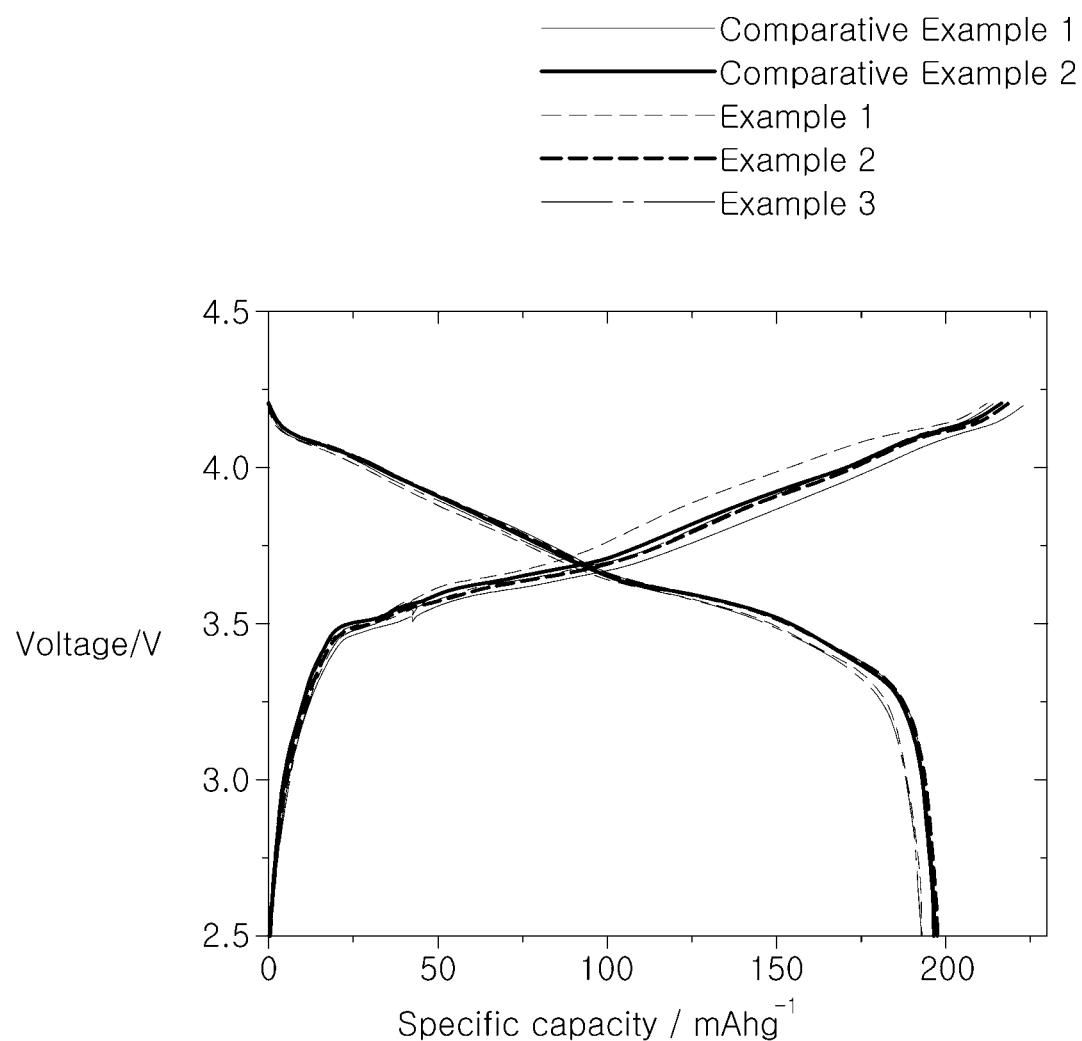
FIG. 2 is a graph showing the initial cell efficiency for Comparative Examples and Examples.

A graph for this is shown in FIG. 2.

TABLE 2

|  | Additives (% by weight) | | | High-temperature lifespan |
| --- | --- | --- | --- | --- |
|  | Additive 1 | $LiPO_2F_2$ | Additive 2 | @100 cycle |
| <Comparative Example 1> | 1.0. | — | — | 90.8% |
| <Comparative Example 2> | 1.0. | 0.5. | — | 90.9% |
| <Example 1> | 1.0. | — | 0.1. | 92.0% |
| <Example 2> | 1.0. | — | 0.5. | 92.4% |
| <Example 3> | 1.0. | — | 1.0. | 90.9% |

Table 2 shows a high-temperature life for Comparative Examples and Examples and shows how much charging/discharging capacity may be maintained compared to an initial charging/discharging capacity after 100 cycles of charging and discharging are repeated. The cut-off voltage was set to 2.5 V to 4.2 V, and the C-rate was tested at 1C at 45° C.

As a result of the experiment, in the case of Example 2 in which 0.1% by weight of additive 2 was added, it was confirmed that the initial cell efficiency was the best. Example 1 showed a high-temperature lifespan similar to that of Comparative Example 2, and Example 3 showed a high-temperature lifespan lower than that of Comparative Examples.

Figure 3:
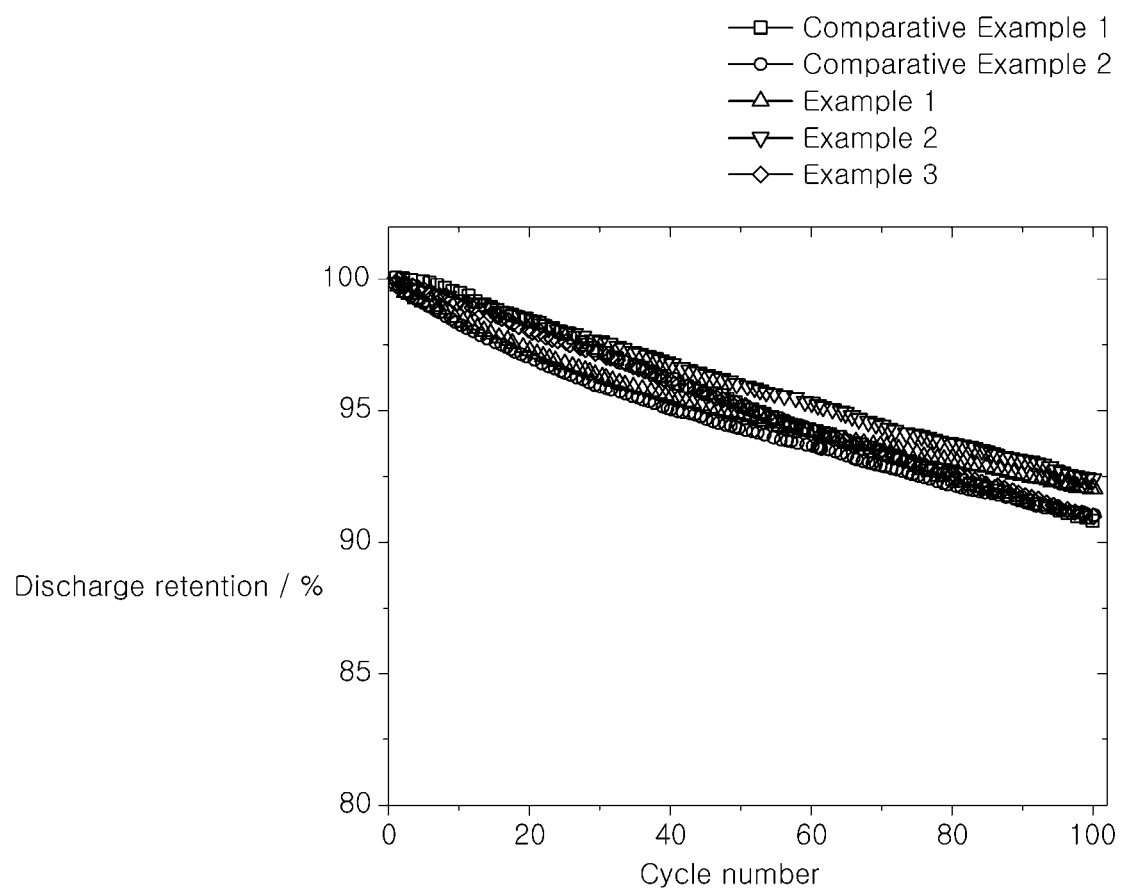
FIG. 3 is a graph showing the high-temperature life for Comparative Examples and Examples.

A graph for this is shown in FIG. 3.

TABLE 3

| | Additives (% by weight) | | | Rate-specific characteristics |
|---|---|---|---|---|
| | Additive 1 | LiPO$_2$F$_2$ | Additive 2 | @2 C-rate |
| <Comparative Example 1> | 1.0. | — | — | 85.7% |
| <Comparative Example 2> | 1.0. | 0.5. | — | 86.1% |
| <Example 1> | 1.0. | — | 0.1. | 86.3% |
| <Example 2> | 1.0. | — | 0.5. | 87.1% |
| <Example 3> | 1.0. | — | 1.0. | 87.0% |

Table 3 shows the rate-specific characteristics for Comparative Examples and Examples and shows how much charge/discharge capacity can be maintained compared to the existing 1C-rate by increasing the rate by 2 times compared to other experiments. Likewise, the cut-off voltage was set to 2.5 V to 4.2 V, and the experiment was performed at 45° C.

As a result of the experiment, in the case of Example 2 in which 0.1% by weight of additive 2 was added, it was confirmed that the initial cell efficiency was the best.

Figure 4:
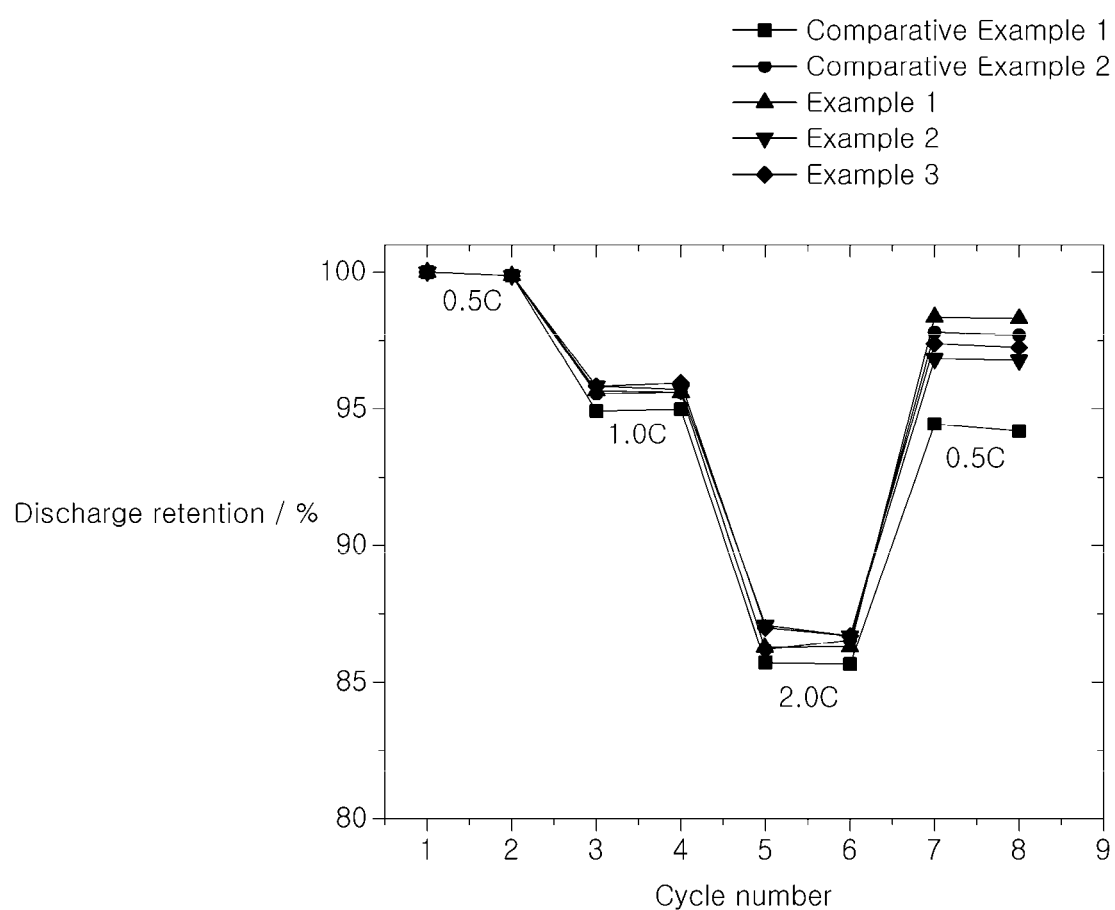
FIG. 4 is a graph showing high rate characteristics for Comparative Examples and Examples.

A graph for this is shown in FIG. 4.

Through the above experiment, when a lithium secondary battery is manufactured using an electrolyte solution using both additive 1 and additive 2, a lithium secondary battery with improved electrochemical properties can be obtained. This is presumed to be due to the fact that additive 2 strongly forms CEI and SEI at the cathode and anode.

From the experimental results, it was confirmed that additive 1 and additive 2 showed the highest electrochemical properties when added in a ratio of 2:1.

Although shown and described with respect to specific embodiments of the present disclosure, it is within the art that the present disclosure can be variously improved and changed without departing from the spirit of the present disclosure provided by the following claims. It will be obvious to those of ordinary skilled in the art.

The invention claimed is:

1. An electrolyte solution for a lithium secondary battery, the electrolyte solution comprising:
   an electrolyte salt; and
   an organic solvent;
   wherein the electrolyte solution further comprises, as additives, vinylene carbonate (VC) represented by Formula 1:

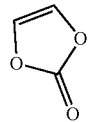

and 4-(allyloxy)phenyl fluoro sulfate represented by Formula 2:

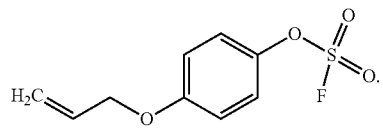

2. The electrolyte solution of claim 1, wherein the 4-(allyloxy)phenyl fluoro sulfate comprises 0.1 to 1.0% by weight with respect to the total weight of the electrolyte solution.

3. The electrolyte solution of claim 1, wherein the VC comprises 0.1 to 10% by weight with respect to the total weight of the electrolyte solution.

4. The electrolyte solution of claim 1, wherein the 4-(allyloxy)phenyl fluoro sulfate and the VC are added in a ratio of 1:2.

5. The electrolyte solution of claim 1, wherein the electrolyte salt is any one compound or a mixture of two or more compounds selected from the group consisting of: LiPF$_6$, LiBF$_4$, LiClO$_4$, LiCl, LiBr, LiI, LiB$_{10}$Cl$_{10}$, LiCF$_3$SO$_3$, LiCF$_{3.0}$CO$_2$, Li(CF$_3$SO$_2$)$_{3.0}$C, LiAsF$_6$, LiSbF$_6$, LiAlCl$_4$, LiCH$_3$SO$_3$, LiCF$_3$SO$_3$, LiN(SO$_{2.0}$C$_2$F$_5$)$_2$, Li(CF$_3$SO$_2$)$_2$N, LiC$_4$F$_9$SO$_3$, LiB(C$_6$H$_5$)$_4$, and Li(SO$_2$F)$_2$N(LiFSI).

6. The electrolyte solution of claim 1, wherein the electrolyte salt is comprised in a concentration range of 0.5 M to 1.0 M.

7. The electrolyte solution of claim 1, wherein the organic solvent is any one or a mixture of two or more solvents selected from the group consisting of: a carbonate-based solvent, an ester-based solvent, an ether-based solvent, and a ketone-based solvent.

8. A lithium secondary battery comprising a cathode, an anode, a separator interposed between the cathode and the anode, and the electrolyte solution of claim 1.

9. The lithium secondary battery of claim 8, wherein the cathode comprises a nickel-cobalt-manganese-based cathode active material.

10. The lithium secondary battery of claim 9, wherein in the cathode active material, nickel, cobalt, and manganese are contained in a ratio of 6:2:2 to 8:1:1.

* * * * *